United States Patent [19]

Weinblatt

[11] Patent Number: 4,649,434

[45] Date of Patent: Mar. 10, 1987

[54] EYEGLASS-FRAME MOUNTABLE VIEW MONITORING DEVICE

[76] Inventor: Lee S. Weinblatt, 797 Winthrop Rd., Teaneck, N.J. 07666

[21] Appl. No.: 572,818

[22] Filed: Jan. 23, 1984

[51] Int. Cl.⁴ .............................................. H04N 5/225
[52] U.S. Cl. .................................... 358/250; 358/225; 358/93; 358/108; 358/901; 340/705
[58] Field of Search ................. 358/200, 250, 88, 225, 358/901, 228, 108, 94, 93; 340/980, 705

[56] References Cited

U.S. PATENT DOCUMENTS 3,568,583  3/1971  Horberg, Jr. et al. .......... 358/108 X
4,310,849  1/1982  Glass ............................... 358/901 X
4,516,157  5/1985  Campbell ............................ 358/108

Primary Examiner—James J. Groody
Assistant Examiner—E. Anne Toth
Attorney, Agent, or Firm—Thomas Langer

[57] ABSTRACT

A device is provided which is specifically adapted to be removably secured to an eyeglass frame as it is worn by a person. The device can be aimed so that an optic system carried by the device will detect the scene being viewed by the wearer.

15 Claims, 2 Drawing Figures

EYEGLASS-FRAME MOUNTABLE VIEW MONITORING DEVICE

BACKGROUND OF THE INVENTION

This invention is related to apparatus for monitoring what a human subject is looking at and, more particularly, to a head-mounted device for detecting at least a portion of the field-of-view of its wearer.

A need exists in various fields to monitor what a person is looking at. For example, in the field of advertising, tests are conducted in which a number of items are placed in front of a subject in order to determine the one to which his attention will be directed. The items, for example, can be packages with each carrying a different design, juxtaposed pages of advertisements, or billboards. In the military field, such a device can be used in pilot training programs for the recording, and later analysis, of the pilot's actions. Also, if connected to a suitable control system, this device can be used to guide a missile all the way to its target by having the pilot merely look at it. In the field of sports, such a monitoring device can be used to analyze a participant's actions. For example, a batter in a slump may not be looking properly at the ball, or a quarterback may not be paying attention to key features of the defense in particular situations. This can be picked up with a device that detects what the player is viewing. These and other applications require a portable, small, light, head-mounted device which can be conveniently worn without interfering with vision or other activities.

Various head-mounted devices already exist which can monitor the view being looked at by the wearer. For example, U.S. Pat. No. 3,542,457 and the publication "Eye Movement Recorder" Series V-0165 by the Polymetric Company disclose view detectors carried by a headband. The publication "Behavior Research Methods & Instrumentation," 1975, Vol. 7(5), includes an article "Survey of Eye Movement Recording Methods," page 405, which shows a face mask and a headband carrying such a device. The same publication, on page 404, shows a helmet-mounted view detector. All of these approaches, however, have certain disadvantages. Helmet-mounted devices are relatively heavy and bulky and may cause tiredness and thus bring on lack of concentration. Also, they interfere somewhat with the wearer's vision. Furthermore, women resist wearing them because it can muss their hair. (One must keep in mind that in advertising testing, for example, the subjects are often volunteers picked at random on the street.) In addition, the helmet does not accomodate eye-glass wearers thus eliminating a large segment of the population from its use. The headband-mounted devices suffer from the same disadvantages as the helmet-mounted ones and, in addition, are difficult to keep in place on the head. If the band is tightened to make it more secure, the pressure may cause headaches. The face mask approach is awkward to wear, also needs to be tight in order to wear it securely which can cause discomfort, and many people perspire heavily under them.

In my U.S. patent application No. 486,031 filed Apr. 18, 1983, I discuss eyeglass-mounted view-monitoring devices. Those embodiments have certain advantages over the helmet-mounted type in being light, compact, and more convenient (at least for women, for example). Also, eyeglass wearers can be accomodated. However, since in that application the view-monitoring device is permanently attached to the frame, for each eyeglass wearer a set of lenses of suitable prescription must be inserted into the frame. This requires that an inventory of lenses be kept on hand. Also, since the frame is not the subject's own, some degree of discomfort during wear is to be expected.

SUMMARY OF THE INVENTION

To overcome these and other disadvantages of the prior art, it is a primary object of the present invention to provide a view monitoring device that can be mounted on any eyeglass frame.

Another object of the present invention is to provide a light, compact device readily mountable on an eyeglass frame.

A further object of the present invention is to provide a view-monitoring device which is mountable on an eyeglass frame and which can be readily aimed and calibrated to suit the individual subject.

Still another object of the present invention is to provide an eyeglass-frame-mountable view monitoring device with an attachment means to enable quickly securing and releasing the device without damaging the eyeglass frame.

Yet another object of the present invention is to provide a view monitoring device which can be readily and removably secured to an eyeglass wearer's own frame.

In providing an apparatus that indicates where a person is looking, the principle is applied that for certain types of viewing head position is adequately representative of what is being looked at. Ideally, eye position should be monitored. However, since eye position monitoring equipment is relatively complex and expensive, it can be dispensed with for certain uses in favor of a device which moves with head motion. When relatively gross eye movement is required to shift from one view to another, a person is much more likely to move the head than the eyes. In the case of food packages on a shelf, for example, the head rather than the eyes is normally moved in scanning the boxes on the shelf. Thus, the head-mounted device of the present invention, when used in such situations, provides an indication of what its wearer is looking at without resort to eye movement monitoring.

The above and other objects of the invention are attained by an apparatus for mounting to the head of a subject wearing eyeglasses to determine what is being viewed by that subject. The apparatus includes a support, and means for releasably securing the support to the eyeglass frame. An optic system is carried on the support, and aiming means are provided for selectively adjusting the direction in which the optic system is aimed.

BRIEF DESCRIPTION OF THE DRAWINGS

The present invention has other objects and advantages which will become more fully apparent in connection with the following detailed description of a preferred embodiment, taken in conjunction with the appended drawings, in which.

DETAILED DESCRIPTION OF THE DRAWINGS

Figure 1:
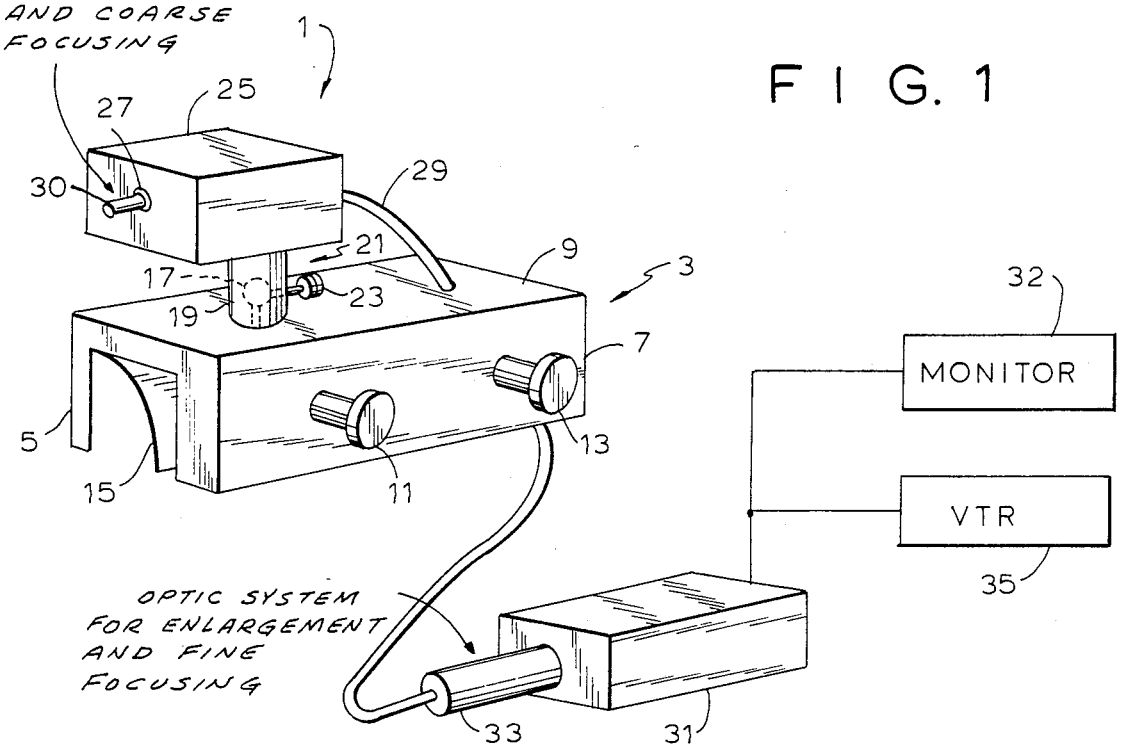
FIG. 1 is a perspective view of the apparatus in accordance with the invention.
Figure 2:
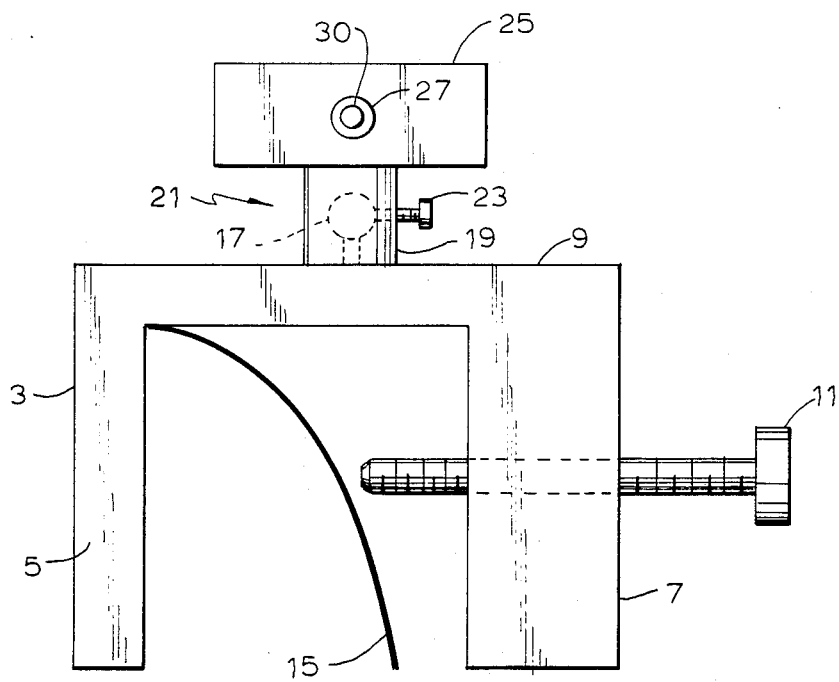
FIG. 2 is a left side view of the apparatus in FIG. 1.

As shown in FIG. 1, the preferred embodiment of eyeglass mounted device 1 includes a U-shaped support bar 3 with legs 5 and 7 and crosspiece 9. In use, it is in an upside down position just as shown in FIGS. 1 and 2. The temple portion of the eyeglass frame is received in the channel between legs 5 and 7 and crosspiece 9 rests on top of the temple portion for vertical support. For lateral support, screws 11 and 13 are tightened until the framepiece is securely held between the tips of screws 11 and 13 and leg 5. To prevent bending the temple frame, or even marring the finish on it, a spring plate 15 is provided inside, and extending the length of, the channel of support bar 3. It is attached to crosspiece 9 by any suitable means such as by welding or with screws. In its normal position, as best shown in FIG. 2, it curves away from leg 5 to leave a wide space between it and leg 5 for receiving the eyeglass frame. As screws 11 and 13 are tightened, they bear against spring plate 15 which, in turn, is pressed tightly against the frame. The plate 15 thus distributes the pressure exerted by screws 11 and 13 so as not to cause pits in the frame and also serves to prevent scratching of the frame by the screws during insertion and removal of the frame from bar 3. When screws 11 and 13 are loosened, plate 15 springs back toward its normal position.

As will be noticed from FIG. 2, leg 7 of support bar 3 is thicker than leg 5 or crosspiece 9. Since leg 7 must be tapped to cooperate with screws 11 and 13, a certain minimum thickness is needed to obtain a sufficient number of threads. The thickness of leg 7 is, thus, dictated by this factor. However, leg 5 and crosspiece 9 need be only thick enough to provide structural rigidity and strength. Since such thickness is normally less than that of leg 7, a lighter weight device is obtained by keeping leg 5 and crosspiece 9 as thin as possible. This thickness depends then on the materials used. In the preferred embodiment, a thickness of $\frac{1}{8}$ in. is used for the leg 5 and crosspiece 9 while $\frac{1}{4}$ in. is used for leg 7. The height of bar 3 is $\frac{1}{2}$ in. and its length is $1\frac{3}{4}$ in. while the material of choice is aluminum.

Attached to the top of support bar 3 is a ball 17 which cooperates with sleeve 19 to form a ball joint 21. A screw 23 is tapped through sleeve 19. Screw 23 when loosened permits rotation of sleeve 19 on ball 17 until a desired position is reached. Screw 23 can then be tightened to lock ball joint 21 in any desired position.

Sleeve 19 is attached to bar 25 by any conventional means, and may also be integral with it. A hole 27 is provided for the length of bar 25 through which fiber optic 29 is inserted. Fiber optic 29 can be aimed by simply swiveling bar 25 on ball-joint 21. Bar 25, in the preferred embodiment, is $\frac{1}{2}$ in. high, $\frac{3}{4}$ in. long, and $\frac{3}{8}$ in. wide. It is also made of aluminum.

Affixed to the front of fiber optic 29 is a viewing optic system 30 to establish a field-of-view and provide at least coarse focusing. The lenses used are conventional and their specifics are dependent on the use to which device 1 is to be put. For example, a relatively narrow field-of-view is required to view advertisements whereas a wider field-of-view is required for billboards. Accordingly, a discussion of further details of optic system 30 is not deemed necessary.

Fiber optic 29 transmits light to an imaging system including video camera 31 which can be placed at a convenient distance away. Depending on the use to which device 1 is to be put, camera 31 can rest on a stationary support or be carried on the person of the subject. Fiber optic 29 is coupled to video camera 31 via optic system 33. This optic system includes focusing lenses to adapt the image size received from the tip of the fiber optic to that receivable by camera 31. This is a fine focusing adjustment which complements the coarse adjustment available with optic system 30. Both are preferred because the degree of focusing sometimes required is difficult to attain with a single set of focusing lenses. Also, the fine focus adjustment is preferably on the camera end of fiber optic 29 because the necessary adjustment is more conveniently and unobtrusively made away from the face of the subject. Between the focusing lenses and camera 31 are placed enlargement lenses for modifying the field-of-view by a magnification power of 1 to 3. The details of this optic system 33 are not shown in the drawings since the lenses are conventional and their specifics depend on the particular use to which device 1 is to be put.

Fiber optic 29 is run through a hole in cross piece 9. A suitable securing means (not shown) holds the fiber optic in place. A certain amount of slack is provided between bar 25 and the hole in crosspiece 9 to allow as much swiveling movement of bar 25 as is needed. This arrangement is preferred to prevent tension on fiber optic 29 between video camera 31 and crosspiece 9 from misaligning bar 25 and possibly even ripping the fiber optic out of bar 25.

Video camera 31 is connected to TV monitor 32 and video tape recorder 35. The image detected by camera 31 can, thus, be viewable in real time as well as recorded for later viewing and analysis.

In operation, the temple piece of an eyeglass frame is secured in support bar 3, as discussed above. Screw 23 is loosened so that fiber optic 29 can be aimed as the operator looks at monitor 32. The subject is asked to look at a particular object and the bar 25 with its fiber optic is swiveled until that object appears in the center of the monitor. The optic systems 30 and 33 are then used to focus, enlarge or reduce what is seen on the monitor to establish the desired field-of-view. The field-of-view is changed in size depending on the application. For example, when magazine pages are being viewed, the field-of-view should be confined to approximately the size of the magazine since the surrounding objects are irrelevant and can, therefore, be a distraction during later analysis. Likewise, if supermarket shelves or billboards are involved, the field-of-view would obviously be enlarged commensurately.

As explained above, the disclosed invention is well suited for use by a subject who normally wears eyeglasses. However, should a subject be a non-eyeglass wearer, he would be given an eyeglass frame with no corrective lenses in it and the device 1 would then be secured to it as disclosed above. The eyeglass frame selected for this purpose would be of the most comfortable variety. It would be readily modifiable to the shape of the subject's head features. An inventory of sizes would be kept on hand. Its main purpose, of course, is to serve as a platform for device 1 without inconveniencing the subject.

Although various specifics for the construction and arrangement of the invention are disclosed above, it is to be understood that these are related to the preferred embodiment. Various modifications can be made which are within the scope of the invention as defined by the claims. For example, ball joint 21 need not have a fastener screw 23 for tightening it into a fixed position. This can be done by simply having a tight fit between sleeve 19 and ball 17 so that no movement between them occurs unless significant force by the operator is applied. Also, device 1 can be made of a plastic or other sturdy, light material. Furthermore, different dimensions than those disclosed above can be used. These and other modifications are readily apparent and, as such, are all included within the spirit and scope of the following claims.

I claim:

1. Apparatus for monitoring the view being looked at by a person wearing eyeglasses, and including a viewing optic system for mounting to said eyeglasses to provide an image to an imaging system remote from said eyeglasses, said eyeglasses including a frame and a temple piece, the viewing optic system comprising;

a support;

quick-release means for releasably yet firmly securing said support to the temple piece of substantially any type of ordinary eyeglasses;

optic system means carried on said support for viewing an image and being associated with said remote imaging system; and aiming means for selectively adjusting the optic system means relative to the eyeglasses to thereby modify the direction in which the optic system is aimed.

2. The apparatus of claim 1 wherein said support is a bar with a U-shaped cross section defining a channel and adapted to receive the temple piece of said eyeglasses in the channel.

3. The apparatus of claim 2 wherein one of the legs of said bar is thicker than the other and wherein said releasable securing means is a screw means tapped into the thicker leg of said bar which when tightened presses the frame against the other leg.

4. The apparatus of claim 2 further including a plate in the channel of said U-shaped bar positioned between the releasable securing means and said temple piece.

5. The apparatus of claim 4, wherein said aiming means comprises an adjustable joint having a ball attached to the support bar and a sleeve secured to the aiming means, said sleeve and ball forming a ball joint.

6. The apparatus of claim 5 further comprising an imaging system remote from said eyeglasses, wherein said optic system means is optically coupled to said imaging system by a fiber optic having one end secured to the aiming means and its other end coupled to a video camera in said imaging system.

7. The apparatus of claim 6, wherein said optic system means further comprises coarse focusing means on said one end of the fiber optic.

8. The apparatus of claim 7, further comprising fine focusing means between the other end of said fiber optic and said video camera.

9. The apparatus of claim 8, further comprising optic enlargement means coupled to said optic system means.

10. The apparatus of claim 1 further comprising an imaging system remote from said eyeglasses, wherein said optic system means is optically coupled to said imaging system by a fiber optic having one end secured to the aiming means and its other end coupled to a video camera in said imaging system.

11. The apparatus of claim 10, wherein said optic system means further comprises coarse focusing means on said one end of the fiber optic.

12. The apparatus of claim 11, further comprising fine focusing means between the other end of said fiber optic and said video camera.

13. the apparatus of claim 12, further comprising optic enlargement means coupled to said optic system means.

14. The apparatus of claim 13, further comprising a video monitor and a video recorder connected to the output of said video camera.

15. The apparatus of claim 9 further comprising a video monitor and a video recorder connected to the output of said video camera.

* * * * *